(12) United States Patent
Matsuda et al.

(10) Patent No.: US 7,150,858 B2
(45) Date of Patent: Dec. 19, 2006

(54) CENTRIFUGAL SEPARATOR

(75) Inventors: Takeshi Matsuda, Kyoto (JP); Shigeru Kitamura, Kyoto (JP); Seiji Satake, Kyoto (JP); Hideki Tanji, Kyoto (JP)

(73) Assignee: Arkray, Inc., Kyoto (JP)

( * ) Notice: Subject to any disclaimer, the term of this patent is extended or adjusted under 35 U.S.C. 154(b) by 538 days.

(21) Appl. No.: 10/344,644

(22) PCT Filed: Aug. 14, 2001

(86) PCT No.: PCT/JP01/07022

§ 371 (c)(1),
(2), (4) Date: Feb. 12, 2003

(87) PCT Pub. No.: WO02/16043

PCT Pub. Date: Feb. 28, 2002

(65) Prior Publication Data

US 2003/0185710 A1 Oct. 2, 2003

(30) Foreign Application Priority Data

| Aug. 18, 2000 | (JP) | ................... 2000-248215 |
| Aug. 18, 2000 | (JP) | ................... 2000-248216 |
| Mar. 8, 2001 | (JP) | ................... 2001-64264 |

(51) Int. Cl.
*G01N 9/30* (2006.01)
*G01N 21/07* (2006.01)

(52) U.S. Cl. .......... 422/72; 422/58; 422/68.1; 422/99; 494/20

(58) Field of Classification Search .......... 422/72, 422/68.1, 58, 99
See application file for complete search history.

(56) References Cited

U.S. PATENT DOCUMENTS

| 3,953,172 | A | * | 4/1976 | Shapiro et al. | ........... 436/500 |
| 4,092,113 | A | * | 5/1978 | Hardy | ........... 436/177 |
| 4,236,666 | A | * | 12/1980 | Aeschlimann et al. | ........ 494/20 |
| 4,244,694 | A | * | 1/1981 | Farina et al. | ........... 436/500 |
| 4,708,940 | A | * | 11/1987 | Yoshida et al. | ........... 436/45 |
| 4,812,294 | A | * | 3/1989 | Combs | ........... 422/72 |
| 5,217,572 | A | * | 6/1993 | Guy et al. | ........... 159/6.1 |
| 5,935,051 | A | | 8/1999 | Bell | |
| 6,060,022 | A | * | 5/2000 | Pang et al. | ........... 422/65 |
| 6,455,002 | B1 | * | 9/2002 | Jokes et al. | ........... 422/63 |
| 6,458,324 | B1 | * | 10/2002 | Schinzel | ........... 422/65 |
| 6,716,395 | B1 | * | 4/2004 | Haystead et al. | ........... 422/72 |
| 6,743,632 | B1 | * | 6/2004 | Clarke et al. | ........... 436/45 |
| 6,872,360 | B1 | * | 3/2005 | Cohen et al. | ........... 422/72 |
| 6,878,342 | B1 | * | 4/2005 | Cole | ........... 422/72 |
| 6,945,129 | B1 | * | 9/2005 | Escal | ........... 73/864.24 |
| 2003/0103870 | A1 | * | 6/2003 | Gazeau et al. | ........... 422/72 |
| 2005/0221972 | A1 | * | 10/2005 | Lurz | ........... 494/43 |

FOREIGN PATENT DOCUMENTS

JP 61-013158 1/1986

(Continued)

*Primary Examiner*—Brian R. Gordon
(74) *Attorney, Agent, or Firm*—Hamre, Schumann, Mueller & Larson, P.C.

(57) ABSTRACT

A centrifugal separator (4), comprising a drive motor (M1), a rotor (41) rotated by the motor (M1) about a specified axis, and a cubette (42) swingably suspended by the rotor (41), wherein the cubette (42) holds a specimen to be tested, the cubette (42) is rotated according to the rotation of the rotor (41) and takes an inclined attitude to a vertical direction and, in this state, the specimen to be tested is centrifugally separated.

16 Claims, 12 Drawing Sheets

FOREIGN PATENT DOCUMENTS

| | | |
|---|---|---|
| JP | 61-150062 | 9/1986 |
| JP | 11-276931 | 10/1999 |

\* cited by examiner

CENTRIFUGAL SEPARATOR

TECHNICAL FIELD

The present invention relates to a centrifugal separator. The present invention also relates to an analyzer provided with a centrifugal separator.

BACKGROUND ART

As is well known, in addition to red cells and white cells, blood contains various components such as glucose, albumin, calcium and the like. Methods for measuring concentrations of these components include an optical method and an electrochemical method. Specifically, a sample (blood) as an analyte is applied to a pad (which is generally worked into an elongated test piece) retaining a reagent, and the resulting reaction is analyzed optically or electrochemically. In the optical method, a portion of the reagent pad which exhibits color reaction is irradiated with light, and the light reflected thereon or the light passing therethrough is analyzed. In the electrochemical method, electrochemical change during the oxidation/reduction reaction occurring in the reagent pad is analyzed with electrodes. Through such analysis, the concentration of a particular component in the blood is determined.

Whichever one of the optical method and the electrochemical method is utilized, to measure the concentration of a component other than blood cells (i.e. blood plasma) while avoiding measurement errors, it is preferable to separate blood plasma from blood cells in advance. Generally, for this purpose, a centrifugal separator is used.

Conventionally, various analyzers incorporating centrifugal separators are proposed for automatically measuring the concentration of a component in blood. An example of such analyzers is disclosed in JP-A-61 (1986)-13158. As shown in FIG. 11 of the accompanying drawings of the present application, the disclosed analyzer (generally indicated by reference number 8) includes a centrifugal separator 9, a pipette unit 80, a constant-temperature bath 81 and an optical measuring unit (not shown).

As shown in FIG. 12, the centrifugal separator 9 includes three rotary discs 90 equally spaced from each other along a hypothetical circumference. The discs 90 are fixed to a rotation shaft 92 via horizontal arms 92. The rotation shaft 92 is rotatable about its axis intermittently at a pitch of 120 degrees. Therefore, each of the discs 90 stopped at one of three stop points A, B and C shown in FIG. 11 moves to a next one of the points.

As shown in FIG. 12, each of the rotary discs 90 is circumferentially provided with a plurality of holes 93 equally spaced from each other. As shown in FIG. 13, a cylindrical container 95 for holding a test tube 94 is pivotally provided in each of the holes 93.

As shown in FIG. 11, the analyzer 8 has an upper surface 82 formed with an opening 83 which is generally equal in diameter to the discs 90, thereby exposing the upper surface of the disc 90 (90a) positioning at the first stop point A. Therefore, the test tubes 94 (FIG. 12) can be easily inserted into the cylindrical containers 95 (FIG. 13) in the discs 90.

After test tubes are inserted into all of the cylindrical containers 95 of the disc 90a, the rotation shaft 91 (FIG. 12) is rotated through 120° to move the disc 90a to the second stop point B. At this point, the disc 90a is rotated at a speed of no less than 3000 rpm to centrifugally separate the sample.

Subsequently, the rotation shaft 91 (FIG. 12) is further rotated through 120° to move the disc 90a to the third point C. The upper surface 82 of the analyzer 8 is formed, at the stop point C, with a pipette insertion hole 84 of a relatively small diameter. At the stop point C, an intended one of the test tubes 94 supported by the disc 90a can be located directly below the pipette insertion hole 84 by intermittently rotating the disc 90a. Thus, supernatant liquid (blood plasma) is taken from each of the test tubes 94 through the pipette insertion hole 84.

The blood plasma thus taken is spotted, through a spotting hole 85, to reagent pads of test pieces (not shown) set in the constant-temperature bath 81. The color reaction occurring at each of the reagent pads is analyzed by the above-described optical method.

Although the above-described prior art analyzer 8 functions properly in many ways, it has the following problems.

Generally; the number of test tubes 94 to be set to the centrifugal separator 9 is not always the same but may vary at each time of the operations for centrifugal separation. Specifically, in one case, all of the cylindrical containers 95 may be loaded with test tubes 94 (containing samples), but in another case, the number of test tubes 94 to be set may be smaller than the number of cylindrical containers 95. In the former case, the center of gravity of the three rotary discs 90 (and the test tubes 94 containing samples) coincides with the axis of the rotation shaft 92. However, in the latter case, the center of gravity of the three rotary discs 90 (and the test tubes 94 containing samples) does not coincide with the axis of the rotation shaft 92. Therefore, the axis deflection of the rotation shaft 92 is likely to occur during the operation, which increases the possibility of the failure of the centrifugal separator 9.

Conventionally, to avoid such a trouble, measures need be taken for keeping the rotation balance of the centrifugal separator when the number of the test tubes 94 containing samples is smaller than the maximum capacity. Specifically, the test tubes 94 need be so set in each rotary disc as to be far from each other as much as possible or a dummy test tube or tubes as a counterbalance need be used.

However, such works are troublesome and considerably deteriorate the efficiency of the sample analysis. Particularly, in a small-scale hospital which has only one or two doctors, it is not advantageous to use the above-described analyzer 8. This is because, generally in such a small-scale hospital, it is not usual to perform blood tests simultaneously with respect to many samples, so that the work for balancing the rotation of the centrifugal separator 9 is almost always necessary. Further, since the prior art analyzer 8 is relatively large, it maybe difficult to find appropriate space for disposing the analyzer in such a small-scale hospital.

DISCLOSURE OF THE INVENTION

The present invention is conceived under the circumstances described above. Therefore, an object of the present invention is to provide a compact analyzer which is capable of efficiently analyzing a single kind of sample at a time.

Another object of the present invention is to provide a centrifugal separator used for such an analyzer.

According to a first aspect of the present invention, there is provided a centrifugal separator including a driving source, a rotor and a swing member. The rotor is rotatable about a rotation axis by the driving source. The swing member is pivotally suspended by the rotor and includes an accommodation space for retaining a separation liquid analyte.

Preferably, the rotor has a center of gravity which is offset from the rotation axis. The center of gravity of the assembly made up of the rotor and the swing member coincides with the rotation axis when the rotor is rotated while pivoting the swing member through a predetermined angle with a predetermined amount of separation liquid analyte contained in the accommodation space.

Preferably, the swing member is removable from the rotor.

Preferably, the swing member is provided with a pair of shaft portions projecting therefrom whereas the rotor is provided with an engagement member for engagement with the shaft portions.

Preferably, the engagement member includes a pair of guides spaced from each other, and each of the guides includes a cutout for receiving the shaft portion and an inclined surface connected to the cutout.

Preferably, the swing member includes an upper opening and a bevel portion tapering toward the upper opening.

Preferably, the swing member includes a container defining the accommodation space and a lid attached to the container, and the upper opening is formed at the lid. The lid includes a rim which is connected to the upper opening and which has a constant diameter.

Preferably, the rotor is provided with a stopper for restricting the pivot angle of the swing member relative to the rotor.

Preferably, the swing member has a vertical axis which coincides with the rotation axis of the rotor when the rotor is not rotated.

Preferably, the swing member has a vertical axis which is offset from the rotation axis of the rotor when the rotor is not rotated.

Preferably, the rotor includes a bottom surface, and a side surface formed with a cutout.

Preferably, the centrifugal separator further comprises a detecting unit for detecting the number of rotations of the rotor and a determination unit for determining whether or not the center of gravity of the rotor during the rotation is offset from the rotation axis based on the data obtained by the detecting unit.

Preferably, the determination unit determines that the center of gravity is offset when the number of rotations of the rotor has not reached a predetermined value after lapse of a predetermined time since the rotor started to rotate.

Preferably, the centrifugal separator further comprises a stopping unit for stopping the rotation of the rotor when the determination unit determines that the center of gravity of the rotor during the rotation is offset.

According to a second aspect of the present invention, there is provided an analyzer comprising a centrifugal separator, a pipette unit, a measurement unit and a positioning mechanism. The centrifugal separator includes a rotor rotatable about a rotation axis and a separation container pivotally suspended by the rotor. The pipette unit sucks a liquid sample contained in the separation container and supplies the sucked sample onto a reagent. The measurement unit, if based on optical principles, irradiates the reagent with light and measures the reflected light or transmitted light. The positioning mechanism moves the rotor to a predetermined position after centrifugal separation is completed. A predetermined amount of liquid sample is retained in the separation container in advance. When the rotor in this state is rotated while pivoting the separation container through a predetermined, the center of gravity of the assembly made up of the rotor and the separation container coincides with the rotation axis.

Preferably, the positioning mechanism includes a detecting unit for detecting whether or not a positioning portion provided at the rotor in advance is deviated, rotor rotating means for rotating the rotor when the positioning portion is deviated, a driving mechanism for moving the rotor in a direction perpendicular to the rotation axis of the rotor, and a stopper member which is movable vertically in accordance with the movement of the rotor by the driving mechanism.

Preferably, the analyzer further comprises a slide table and a casing movable on the slide table by the driving mechanism. The rotor is held by the casing. The slide table includes a higher flat surface and a lower flat surface. The stopper member moves vertically by coming into engagement with the higher flat surface or the lower flat surface in accordance with the movement of the casing.

Preferably, the rotor is provided with an engagement hole. The stopper member is inserted into the engagement hole to positionally fix the rotor.

Preferably, the engagement hole is tapered for facilitating the insertion of the stopper member.

BEST MODE FOR CARRYING OUT THE INVENTION

Preferred embodiments of the present invention will be described below in detail with reference to the accompanying drawings.

Figure 1:
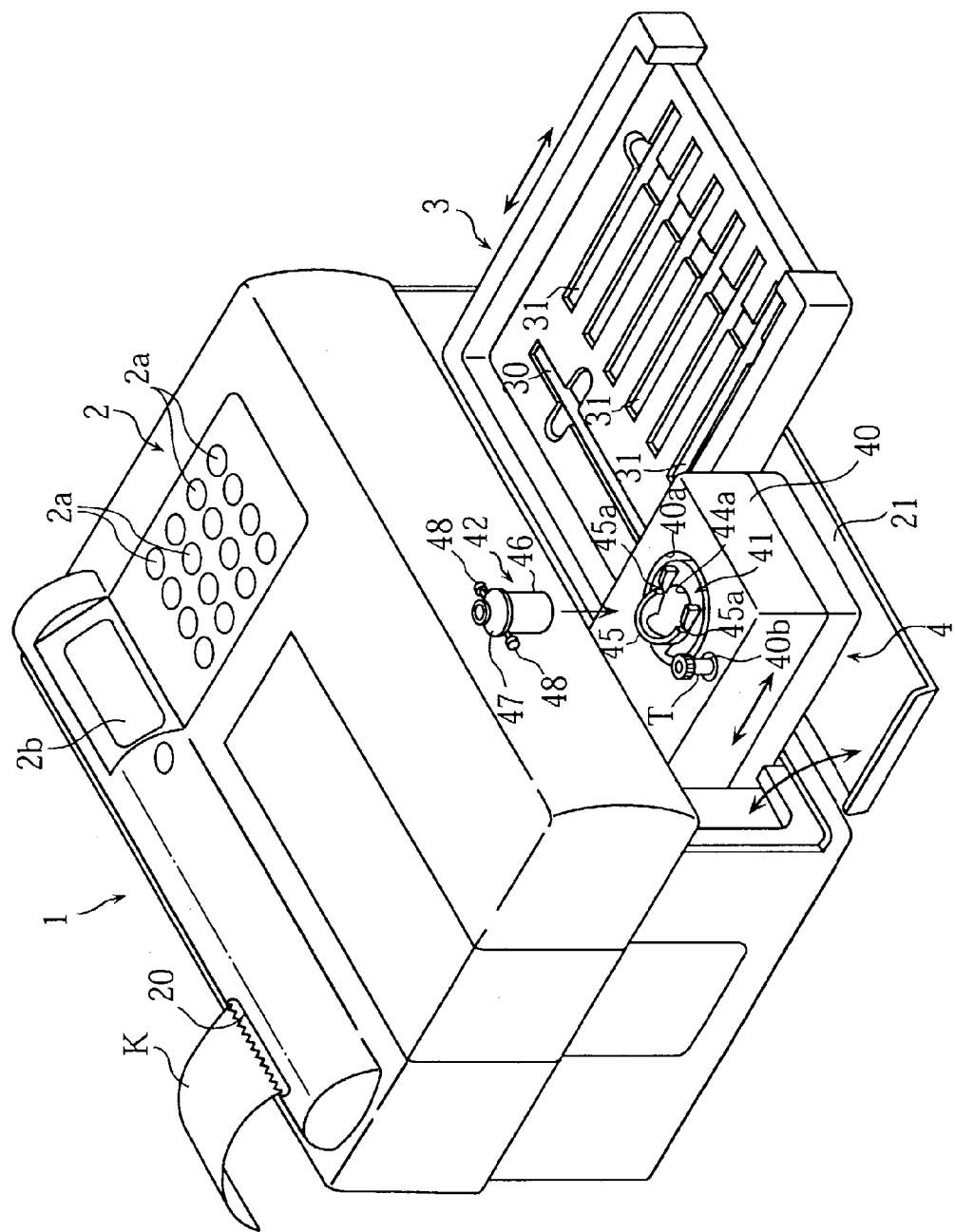
FIG. 1 is a perspective view illustrating an analyzer according to a first embodiment of the present invention.
Figure 2:
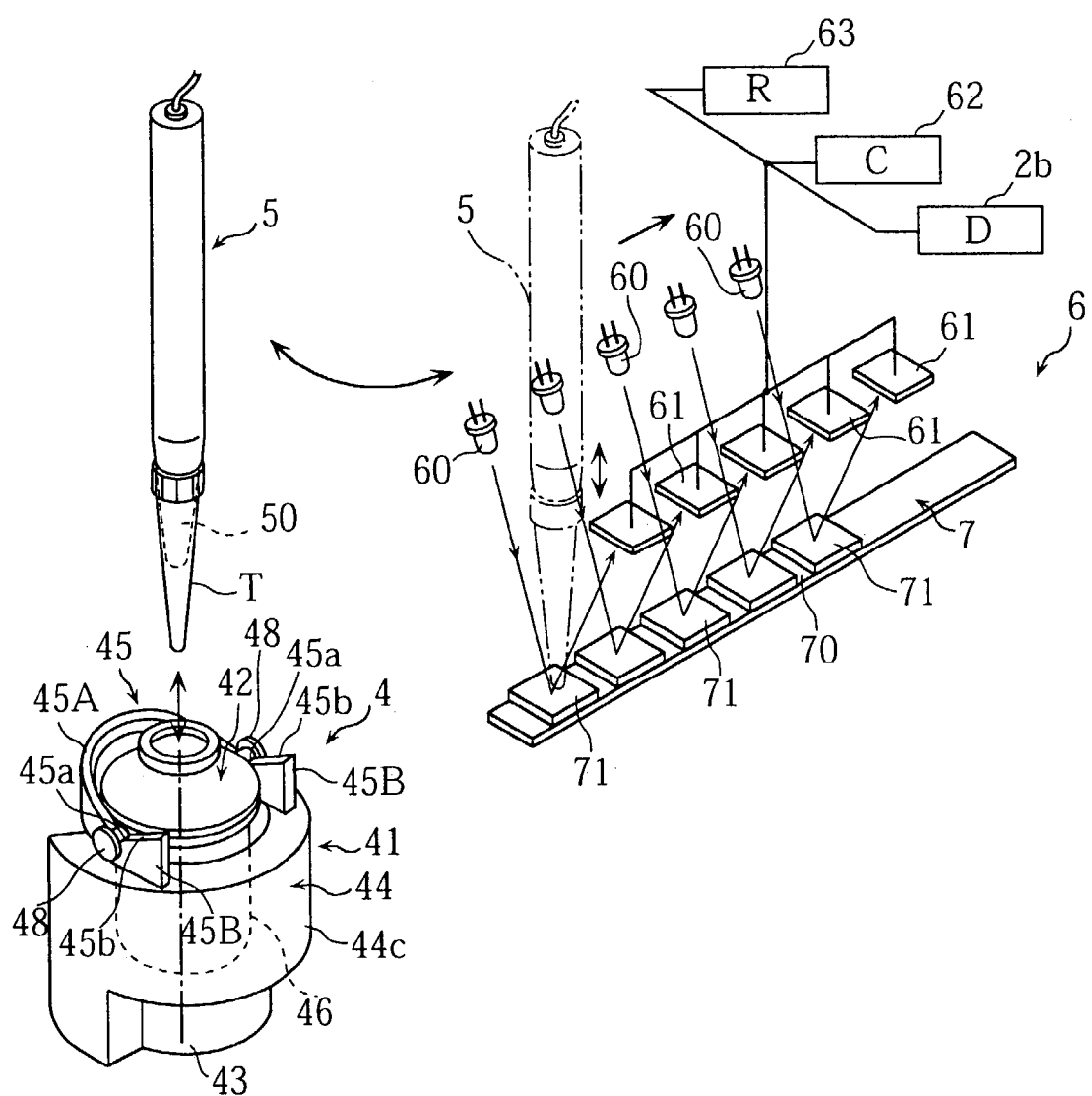
FIG. 2 illustrates a pipette mechanism and an optical measurement unit used for the analyzer of the first embodiment.

FIGS. 1–6 illustrate a bio-sample analyzer (generally indicated by reference numeral 1) according to a first embodiment of the present invention. The analyzer 1 functions to measure the concentration of a particular component (e.g. glucose, albumin or calcium) contained in blood. As shown in FIGS. 1 and 2, the analyzer 1 includes a housing 2, a test piece mount 3, a centrifugal separator 4, a pipette unit 5 and an optical measurement unit 6.

As shown in FIG. 1, the housing 2 has an upper surface provided with various kinds of operation buttons 2a, a display 2b and a discharge port 20 for a recording paper K. The operation buttons 2a are provided for setting measurement conditions and for controlling the operation of the analyzer 1. The display 2b displays the measurements or the operation results of the operation buttons 2a. The recording paper K, which may be thermosensitive paper, is used for recording the measurements.

The housing 2 is provided, on the front side thereof, with a door 21 for opening and closing movement. When the door 21 is closed, the test piece mount 3 and the centrifugal separator 4 are housed in the housing 2. When the door 21 is opened, the test piece mount 3 and the centrifugal separator 4 can be pulled out from the housing 2, as shown in FIG. 1.

The test piece mount 3 is provided for disposing a test piece 7 (See FIG. 2). The illustrated test piece 7, which is designed for measuring plural components, comprises a base member 70 in the form of a strip and a plurality of (five in FIG. 2) reagent pads 71 provided on the strip. Each of the reagent pads 71 is impregnated with a reagent which exhibits color reaction upon contacting one of the substances to be measured, such as glucose, albumin or calcium. Instead of the illustrated example, use may be made of a test piece for measurement of a single component which includes a single reagent pad on a single base member. The test piece 7 for measurement of plural components is retained in a first slit 30 of the test piece mount 3. As shown in FIG. 1, the first slit 30 is elongated in a direction perpendicular to the sliding direction of the test piece mount 3. On the other hand, the test piece for measurement of a single component is retained in one of second slits 31 (six slits illustrated in the figure) of the test piece mount 3. Each of the second slits 31 is elongated in a direction parallel to the sliding direction of the test piece mount 3.

Figure 3:
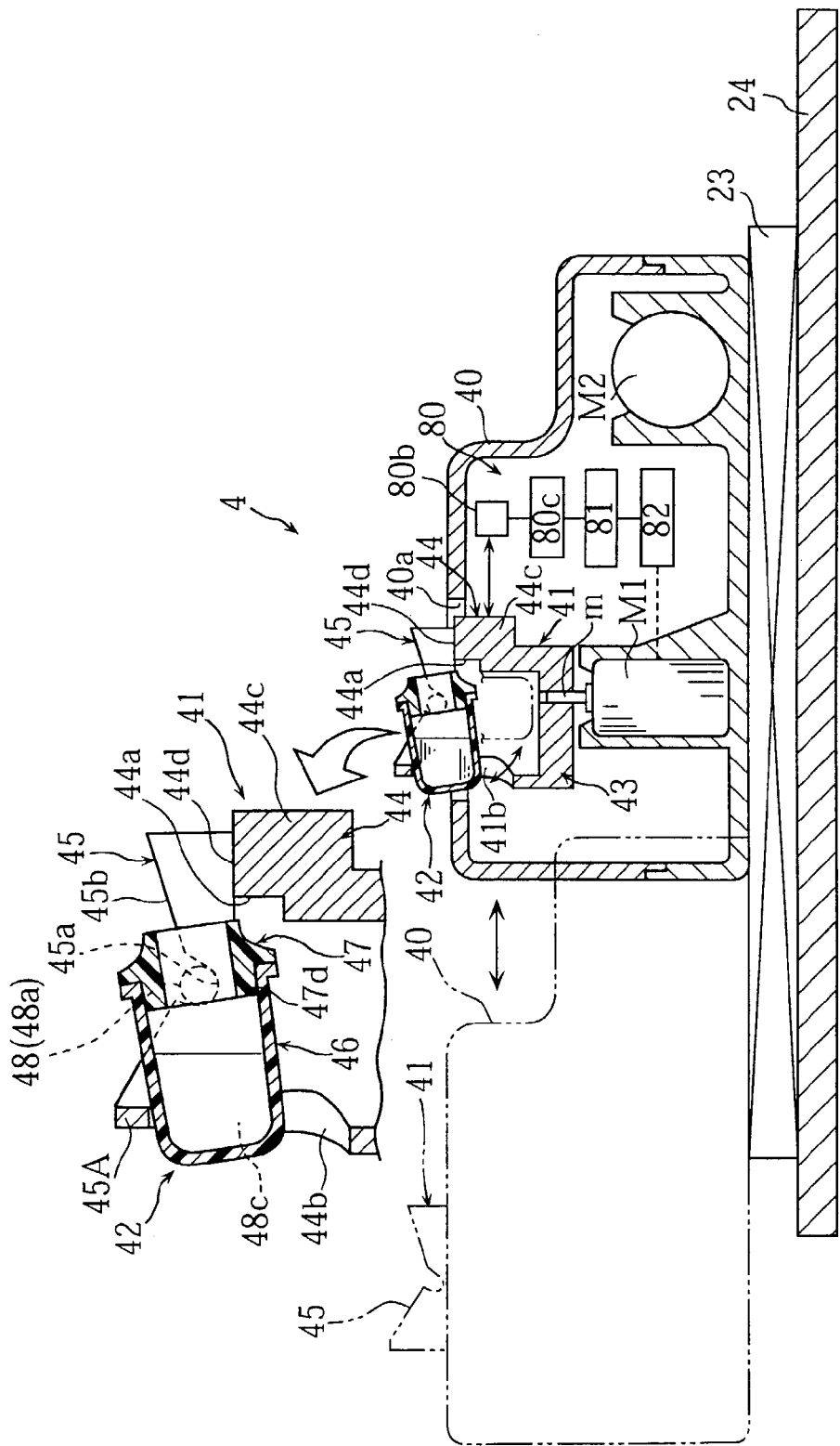
FIG. 3 illustrates a centrifugal separator unit for use in the analyzer of the first embodiment.

As shown in FIG. 3, the centrifugal separator 4 includes a casing 40, a rotor 41, a cuvette 42, a detecting unit 80, a determination unit 81 and a stopping unit 82. As will be described later, the cuvette 42 is removably attached to the rotor 41.

The casing 40 has an upper surface formed with a through-hole 40a. Directly below the through-hole is arranged a DC motor M1. The motor M1 has an output shaft m to which the bottom wall 43 of the rotor 41 is fixed. Therefore, when the motor M1 is driven, the rotor 41 rotates about the axis of the output shaft m. As shown in FIG. 1, beside the through-hole 40a, a tip set unit 40b is provided for holding a tip T to be mounted to the pipette unit 5 (See FIG. 2).

As shown in FIG. 3, the casing 40 is reciprocally slidable on a slide table 24 by a known driving mechanism 23. The driving mechanism 23 may be a rack-and-pinion actuator, for example. In this case, a pinion (not shown) is pivotally mounted to the casing 40, whereas a rack (not shown) for meshing with the pinion is fixed to the slide table 24. The casing 40 houses a reversely rotatable motor M2 having a rotation shaft connected to the pinion. With this structure, when the door 21 of the housing 2 is open, it is possible to automatically pull out the centrifugal separator 4 from the housing 2 or to automatically put the centrifugal separator into the housing 2.

Figure 4:
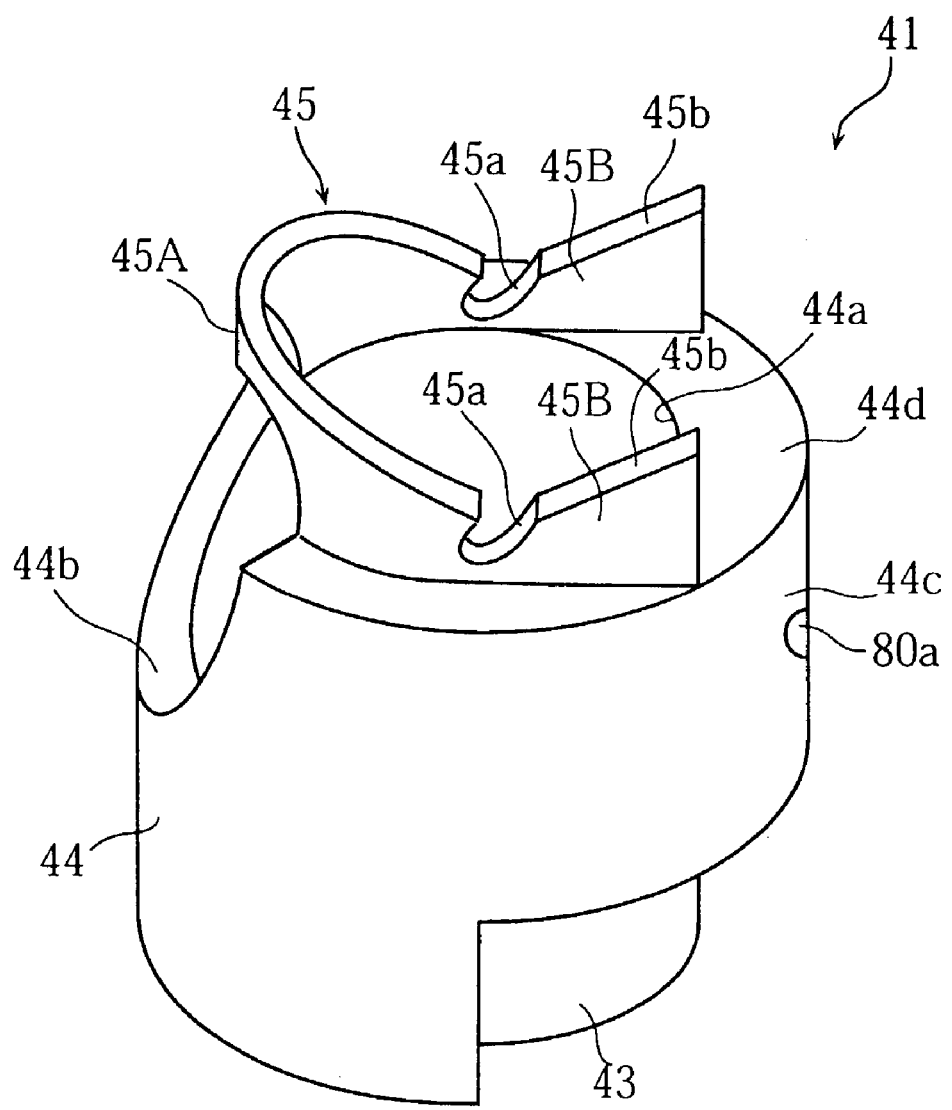
FIG. 4 is a perspective view illustrating a rotor for use in the centrifugal separator unit of FIG. 3.

As shown in FIGS. 3 and 4, the rotor 41 has a circumferential wall 44 formed with a cutout 44b connected to an upper opening 44a. The rotor is further provided with a bulging portion 44c on the opposite side of the cutout 44b. Therefore, the center of gravity of the rotor 41 is offset toward the bulging portion 44c by a predetermined amount. The offset amount is so set that the cuvette 42 containing a predetermined amount of blood rotates stably together with the rotor 41 about the axis of the rotor when the motor M1 is driven at a predetermined rotation speed. Therefore, according to the illustrated embodiment, a conventionally used counterbalance is not necessary, and centrifugal separation of a sample can be performed using only a single cuvette.

The bulging portion 44c is provided with a mark 80a which constitutes part of the detecting unit 80. Details of the detecting unit 80 will be described later.

The rotor 41 has an upper surface 44d provided with a positioning crown 45. As shown in FIG. 4, the positioning crown 45 includes a pair of guides 45B and a bridge 45A. The bridge 45A extends above the cutout 44b. The guides 45B are spaced from each other with the upper opening 44a located therebetween. Each of the guides 45B includes a bearing portion 45a and an inclined surface 45b. The bearing portion 45a is provided generally centrally of the guide 45B. The lower end of the inclined surface 45b is connected to the bearing portion 45a.

The rotor 41 having the above-described structure may be formed by making an intermediate casting from aluminum and then mechanically working the intermediate casting. The weight of the rotor 41 may be about 20 grams.

Figure 5:
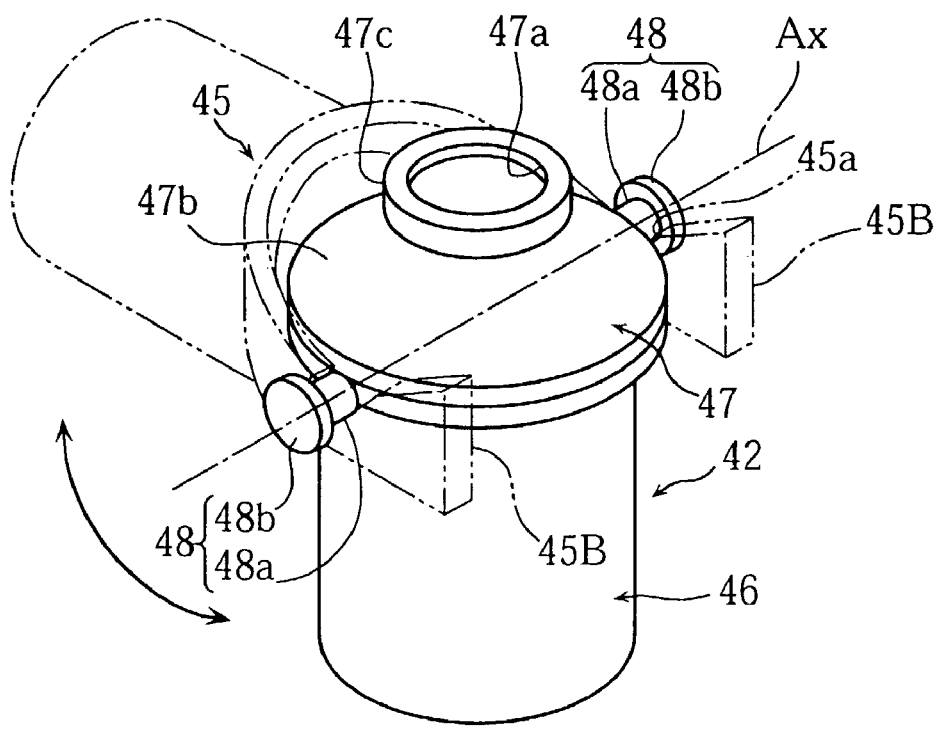
FIG. 5 illustrates a separation container for use in the centrifugal separator unit of FIG. 3.

As shown in FIG. 5, the cuvette 42 includes a main body 46 and a lid 47. The main body 46 is in the form of a bottomed cylinder having an accommodation space 48c (See FIG. 6). The main body 46 has a side wall from which a pair of arms 48 extend in opposite directions from each other. Each of the arms 48 includes a shaft 48a and an engagement portion 48b. The two shafts 48a have a common axis Ax. Each of the shafts 48a has a diameter which generally coincides with the width of the bearing portions 45a. Each of the engagement portions 48b has a diameter which is larger than the width of the bearing portions 45a. The arms 48 are pivotally received in the bearing portions 45a. As a result, the cuvette 41 is pivotable about the axis Ax relative to the rotor 41.

Figure 6:
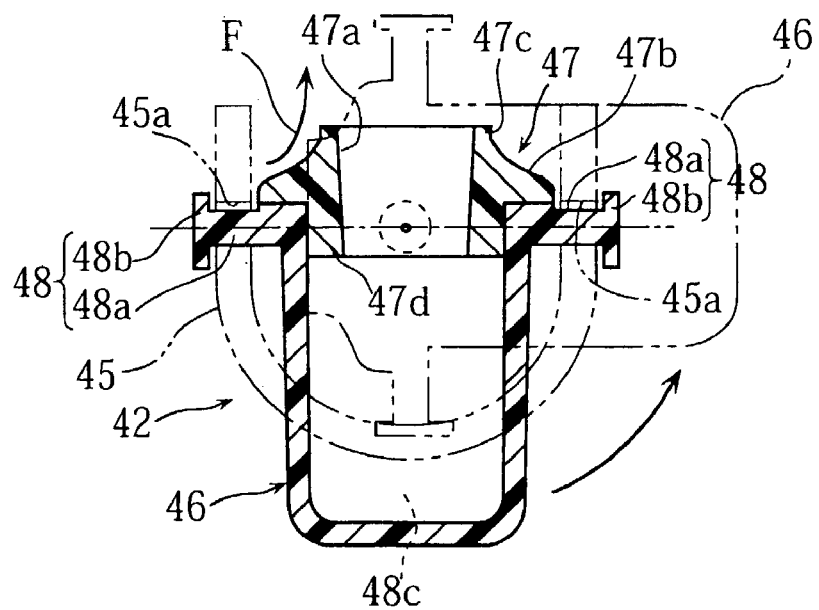
FIG. 6 illustrates the rotation of the separation container of FIG. 5.

As shown in FIGS. 5 and 6, the lid 47 includes a central opening 47a, a bevel portion 47b and a rim 47c. The opening 47a communicates with the accommodation space 48c of the main body 46. The bevel portion 47b is tapered toward the opening 47a. The rim 47c has a constant diameter. The lid 47 further includes an engagement portion 47d (See FIG. 6) projecting downward from the bevel portion 47b. By fitting the engagement portion 47d into the accommodation space 48c of the main body 46, the lid 47 is attached to the main body 46.

The main body 46 and the lid 47 are formed by molding a resin. The length from the bottom of the main body 46 to the arms 48 may be about 10–20 mm. The accommodation space 48c may have a volume of about 300–500μl. The blood sample contained in the main body 46 is separated into blood cells and blood plasma by the centrifugal separation, as described later. At that time, the blood cells precipitate, while the blood plasma becomes a supernatant liquid.

As shown in FIG. 2, the pipette unit 5 includes a nozzle 50 and a tip T for attachment to the nozzle. Though not illustrated, the nozzle 50 is internally provided with a thin elongate pressure generation tube for selectively generating a negative pressure to suck a sample and a positive pressure to discharge a sample. The sucked sample is retained in the space within the tip T but does not contact the nozzle 50. In the illustrated embodiment, the pipette unit 5 takes the supernatant liquid (blood plasma) from the cuvette 42 and applies the liquid to each of the reagent pads 71 of the test piece 7. For this purpose, the pipette unit 5 is movable vertically and horizontally.

As shown in FIG. 2, the optical measurement unit 6 includes a plurality of light emitting elements 60 and a plurality of light receiving elements 61. Each of the light emitting elements 60 may be a light emitting diode (LED), for example. Each of the light receiving elements 61, which may be e.g. a photoelectric conversion element, receives the light reflected by a corresponding one of the reagent pads 71. In the figure, five reagent pads 71 as well as the same number of light emitting elements 60 and the same number of light receiving elements 61 are illustrated. Actually, however, the optical measurement unit 6 includes a larger number of light emitting elements and light receiving elements. Specifically, as described before, the test piece mount 6 can carry one test piece 7 (having five reagent pads 71) for measurement of plural components and six test pieces (each having one reagent pad 71) for measurement of a single component at a time. Therefore, to individually irradiate eleven (=5+1×6) reagent pads 71 with light, eleven light emitting elements 60 are provided. Accordingly, the optical measurement unit 6 includes eleven light receiving elements 61. The light emitting elements 60 and the light receiving elements 61 are fixed in the housing 2.

The detecting unit 80 includes a photosensor 80b and a computing section 80c in addition to the mark 80a.

The mark 80a may be of any form if only it can be irradiated with light in a manner different from the side surface of the rotor 41. For example, the mark 80a may have a reflectivity which is lower or higher than that of the side surface of the rotor 41. The mark 80a may be provided by applying ink or attaching a tape to the side surface of the rotor 41. Alternatively, the mark 80a may be a recess or a projection formed on the side surface of the rotor 41.

The photosensor 80b includes a light emitting element (not shown) and a light receiving element (not shown), which are housed in a single package. The photosensor 80b is of a light-reflective type, and the light emitting face of the light emitting element and the light receiving face of the light receiving element are oriented toward the same direction (toward the rotor 41). As shown in FIG. 2, the light emitted from the light emitting element is reflected by the side surface of the rotor 41, and the reflected light is received by the light receiving element. When the light emitted from the light emitting element becomes incident on the mark 80a, a relatively small (or large) amount of reflected light is detected by the light receiving element. Based on such variation of light reflection amount thus detected, the computing section 80c computes the number of rotations of the rotor 41.

Based on the number of rotations of the rotor 41 thus computed, the determination unit 81 determines whether the balance of the center of gravity of the rotor 41 is properly maintained during the rotation. Specifically, it is determined whether the number of rotations of the rotor 41 has reached a predetermined value after a lapse of predetermined time since the rotor started to rotate. If the number of rotations of the rotor 41 has reached the predetermined value, it is determined that the rotation of the rotor 41 is normal, i.e. the cuvette 42 containing a proper amount of sample is properly set to the rotor 41. On the other hand, if the number of rotations of the rotor 41 has not reached the predetermined value, the rotation of the rotor 41 is determined to be abnormal. In this case, it is determined that the cuvette 42 does not contain a proper amount of sample or the cuvette 42 is not set to the rotor 41.

When the balance of the center of gravity of the rotating rotor 41 is determined to be improper, the stopping unit 82 stops the voltage application to the rotor 41, thereby stopping the rotation of the rotor 41. In this way, when the cuvette 42 is not properly set to the rotor 41, the operation of the centrifugal separator 4 is automatically stopped.

The computing section 80c, the determination unit 81 and the stopping unit 82 may comprise a CPU, a ROM, a RAM and the like for example.

Next, description will be made as to the usage and operation of the analyzer 1 having the above-described structure.

To measure the concentration of a particular component in blood other than blood cells (i.e. glucose, albumin, calcium or the like), the centrifugal separation of blood cells need be performed in the analyzer 1. For this purpose, blood (e.g. 250μm) is injected into the cuvette 42. Then, the cuvette 42 is set to the rotor 41 and the motor M is driven. As a result, the cuvette 42 rotates together with the rotor 41 at high speed (e.g. 14000 rpm) to separate blood cells and blood plasma.

When the cuvette 42 has a length of 10–20 mm and an internal volume of 400–500μl, the rotation (14000 rpm) of the cuvette 42 exerts a centrifugal force of about 1000 G onto the gas/liquid interface in the container while exerting a centrifugal force of no less than 2000 G onto the bottom of the cuvette 42. To properly separate blood cells from blood plasma under such condition, the cuvette 42 need be rotated for 10±5 minutes, for example.

As shown in FIG. 1, the cuvette 42 is set to the rotor 41 in the state where the centrifugal separator 4 is pulled out from the housing 2 after opening the door 21 of the housing 2. Such a state can be provided automatically by pressing a predetermined one of the operation buttons 2a after opening the door 21. In this state, the main body 46 of the cuvette 42 is inserted into the opening 44a of the rotor 41, and the shafts 48a of the cuvette 42 are brought into engagement with the bearing portions 45a of the positioning crown 45. This operation can be performed easily by sliding the shafts 48a along the inclined surfaces 45b (See FIG. 4) of the positioning crown 45.

As shown in FIG. 5, in the non-driven state, the cuvette 42 is suspended by the rotor 41. At that time, the axis of the cuvette 42 generally coincides with the rotation axis of the rotor 41 (See FIG. 2). As shown in FIGS. 3 and 5, when the rotor 41 is rotated, the cuvette 42 pivots about the axis Ax of the shafts 48a due to the centrifugal force. At that time, if no obstacles exist, the cuvette 42 pivots through more than 90 degrees at the maximum. In practice, however, the bridge 45A of the positioning crown 45 of the rotor 41 restricts the pivotal movement of the cuvette 42. Thus, in the illustrated embodiment, the cuvette 42 continues to rotate together with the rotor 41 while keeping the pivot angle of about 80–85 degrees.

The rotation of the cuvette 42 generates airflow along the profile of the lid 47. If no countermeasure is taken, it is probable that the airflow enters the cuvette 42 through the opening 47a. If the airflow enters the cuvette 42, turbulent flow is generated in the cuvette 42 to reduce the air pressure near the opening 47a. Such a state unduly promotes the evaporation of the liquid component contained in the cuvette 42 and is therefore undesirable.

According to the illustrated embodiment, however, such a problem is effectively prevented. As described before, the lid 47 includes the bevel portion 47b tapered toward the opening 47a and the rim 47c having a constant diameter. Therefore, the airflow generated around the outer surface of the lid 47 travels along the path indicated by an arrow F in FIG. 6.

That is, the airflow progresses to be farther from the opening 47a. Therefore, such turbulent flow as described above is not generated in the cuvette 42, so that excessive evaporation of the liquid component in the cuvette 42 can be prevented without the need for closing the opening 47a.

After the centrifugal separation of the sample is completed, the concentration of a particular component is measured automatically. The process for automatic concentration measurement basically includes applying of the supernatant liquid (blood plasma) to a reagent pad 71, optical detection of the color reaction on the reagent pad and computation of the detection result.

Specifically, blood plasma is applied to a reagent pad 71 in the following manner. Firstly, the tip T is attached to the nozzle 50 of the pipette unit 5. The tip T to be attached is in advance set to the tip set unit 40b (See FIG. 1) provided at the casing 40 of the centrifugal separator 4. The nozzle 50 is positioned above the set tip T and then moved downward. In this way, the tip T is automatically attached to the nozzle 50. After the tip T is attached, the test piece 7 as shown in FIG. 2 is disposed on the test piece mount 3, and the test piece mount 3 is housed in the housing 2. Subsequently, as shown in FIG. 2, blood plasma is sucked from the cuvette 42 by using the pipette unit 5 and applied to one of the reagent pads 71 on the test piece 7. Specifically, the pipette unit 5 is first moved above the cuvette 42 suspended by the rotor 41. Then, the pipette unit 5 is moved downward to dip the lower end of the tip T into the blood plasma contained in the cuvette 42. In this state, the air pressure in the nozzle 50 is reduced to generate a negative pressure in the tip T, thereby sucking the blood plasma. The pressure drop in the nozzle 50 may be performed by driving an external pump (not shown) connected to the nozzle 50. The sucked blood plasma is retained in the tip T. Then, the blood plasma is discharged. Specifically, first, the pipette unit 5 is moved above a desired reagent pad 71. Then, the air pressure in the nozzle 50 is increased using the external pump to discharge the taken blood plasma onto the reagent pad 71.

The above-described process of sucking and discharging blood plasma is repetitively performed for each of the reagent pads 71 of the test piece 7.

Subsequently, the color reaction on the reagent pads is detected. Specifically, each of the reagent pads 71 is impregnated with a reagent which appropriately exhibits color reaction in accordance with the concentration of a particular component in the blood plasma. As described before, light emitted from the light emitting elements 60 (FIG. 2) is directed to the respective reagent pads 71 exhibiting color reaction, and the light reflected thereon is received by the respective receiving elements 61 individually. When the light receiving elements comprise photoelectric conversion elements, electric charge corresponding to the received amount of light (i.e. corresponding to the degree of color reaction) is generated at each of the light receiving elements 61. The electric charge is transmitted to a computing section 62.

Based on the electric charge supplied in this way, computation of the detection results is performed. The computing section 62 may comprise a CPU, a ROM, a RAM and the like, for example. The computing section 62 executes programs stored in the ROM to determine the concentration of a particular component based on the amount of light received by the light receiving element 61. Specifically, a calibration curve (function) which correlates a received amount of light with the concentration of a particular component is generated in advance. The concentration of a particular component is determined based on the calibration curve.

The result of computation conducted at the computing section 62 is displayed at a display 2b. Further, the computation result is recorded at a recording section 63 on a recording medium such as a recording paper K or a magnetic card automatically or when the user pressed the predetermined operation button 2a.

Next, with reference to FIGS. 7–10, description will be made as to an analyzer (generally indicated by reference numeral 1') according to a second embodiment of the present invention. In these figures, the elements or portions which are identical or similar to those of the analyzer described with reference to FIGS. 1–6 are designated by the same reference signs as those used for the analyzer, and the description of such elements will be omitted.

The analyzer 1' of the second embodiment differs from the analyzer 1 of the first embodiment in structure of a slide table 24' and a centrifugal separator 4' and in controlling mechanism of a rotor 41'.

Figure 7:
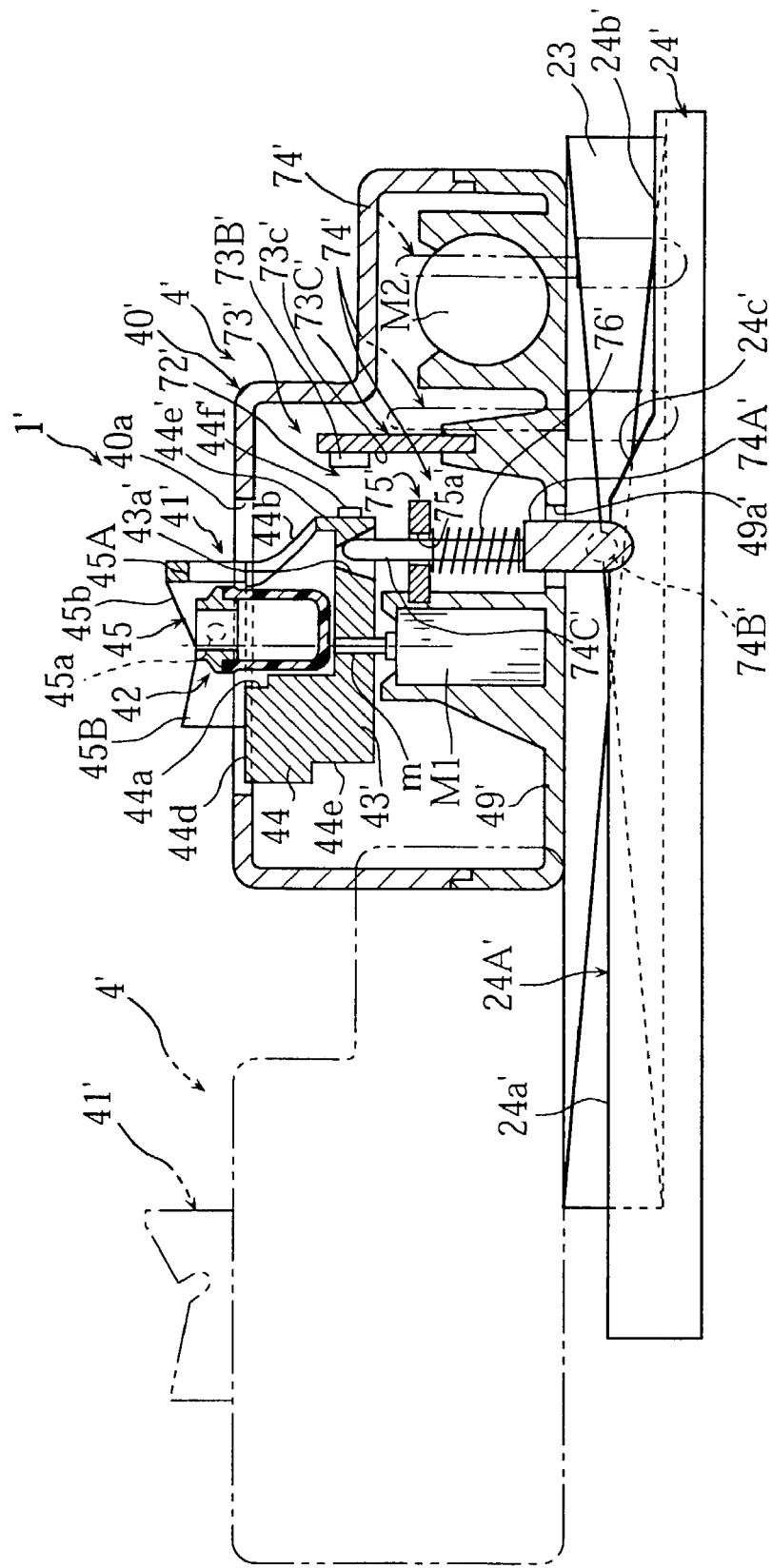
FIG. 7 is a sectional view illustrating an analyzer according to a second embodiment of the present invention.
Figure 9:
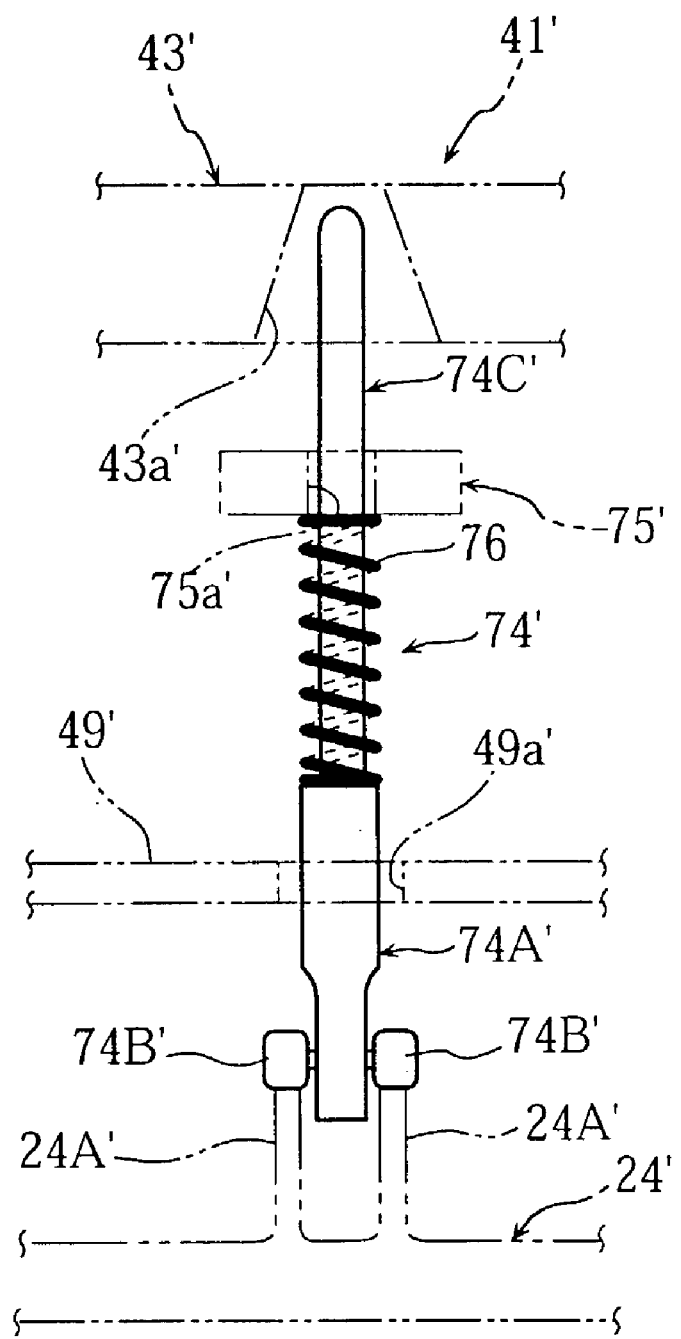
FIG. 9 illustrates a stopper mechanism for use in the analyzer of the second embodiment.
Figure 10:
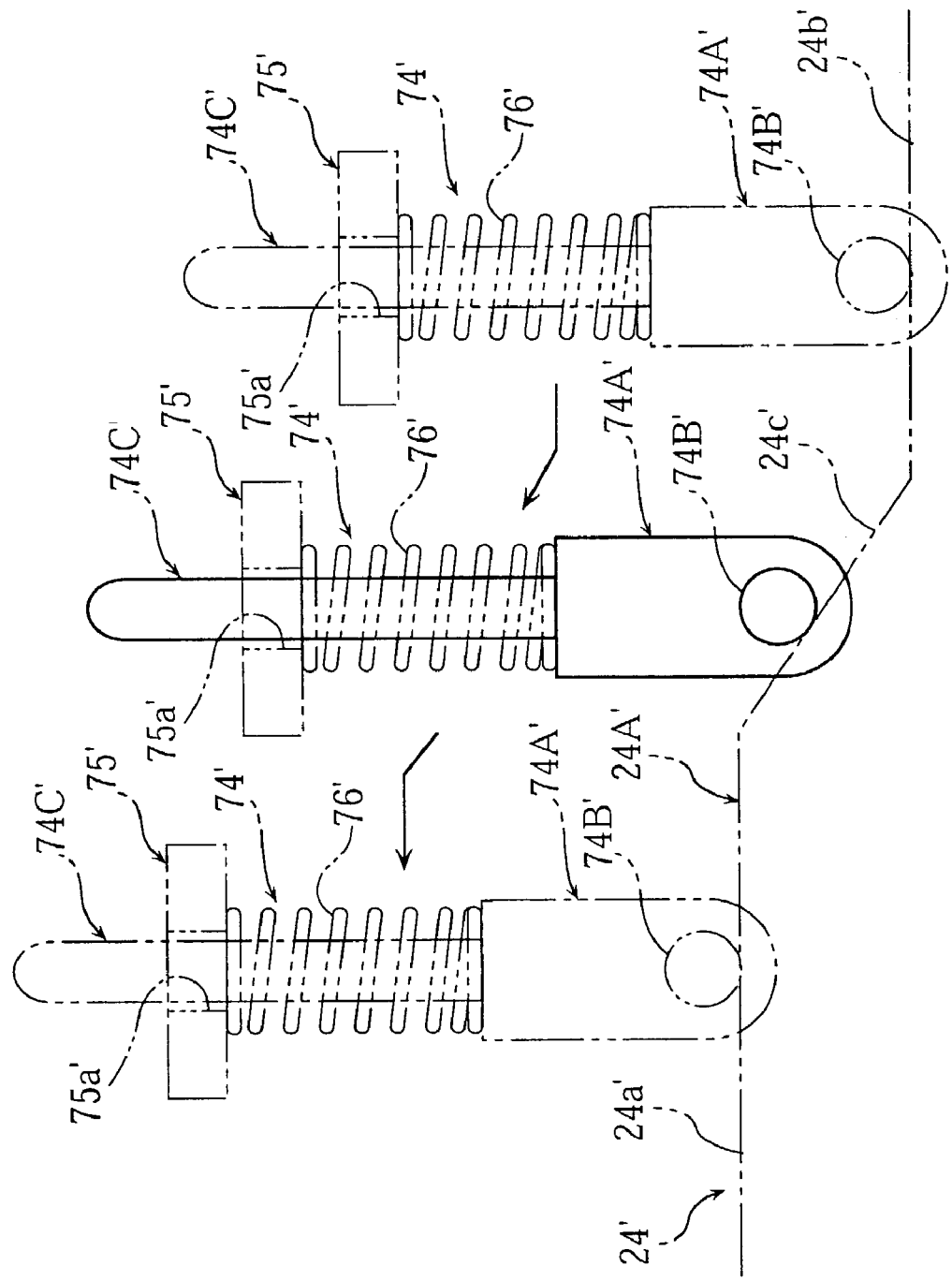
FIG. 10 illustrates the operation of the stopper mechanism of FIG. 9.
Figure 11:
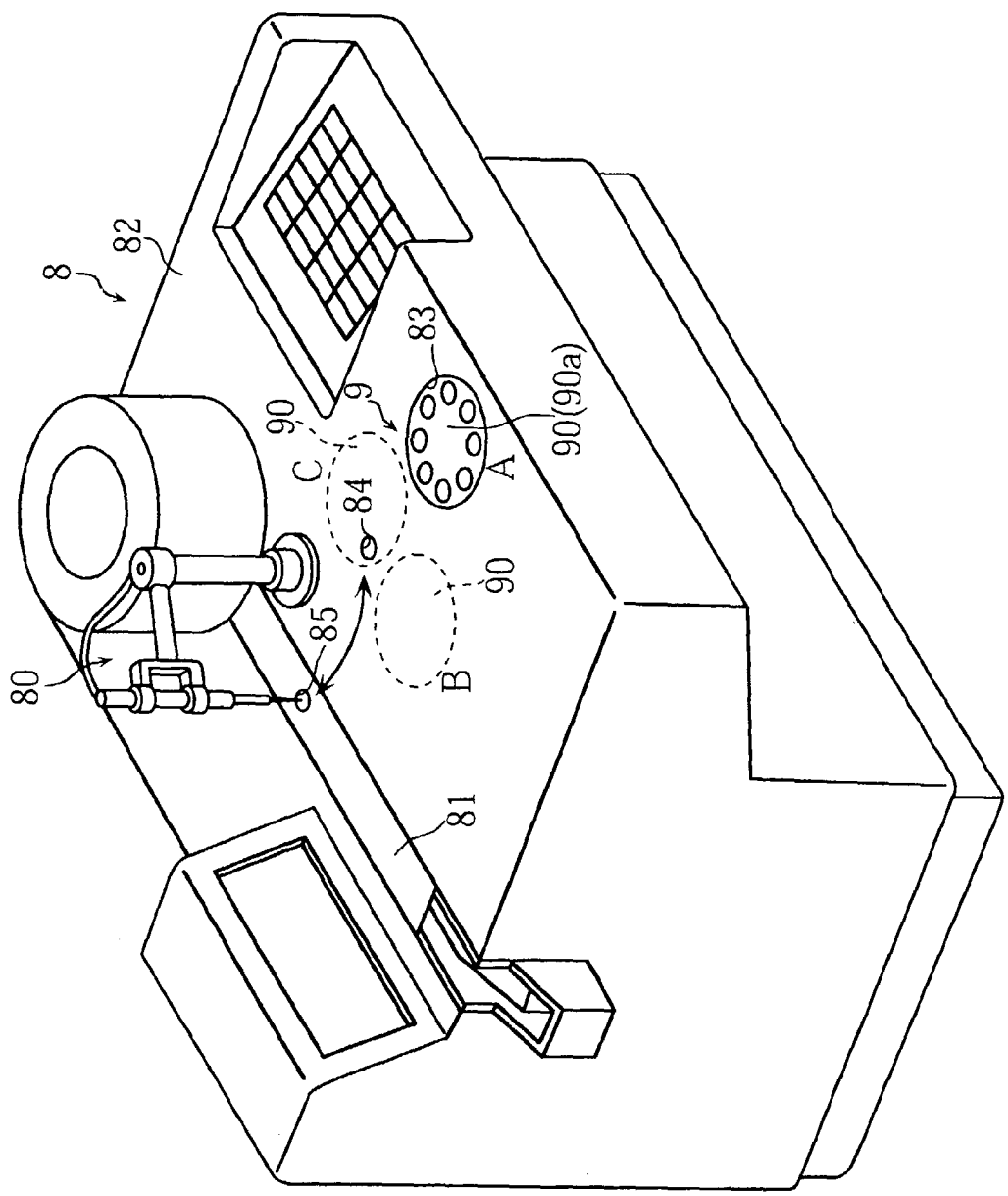
FIG. 11 is a perspective view illustrating a prior art analyzer.
Figure 12:
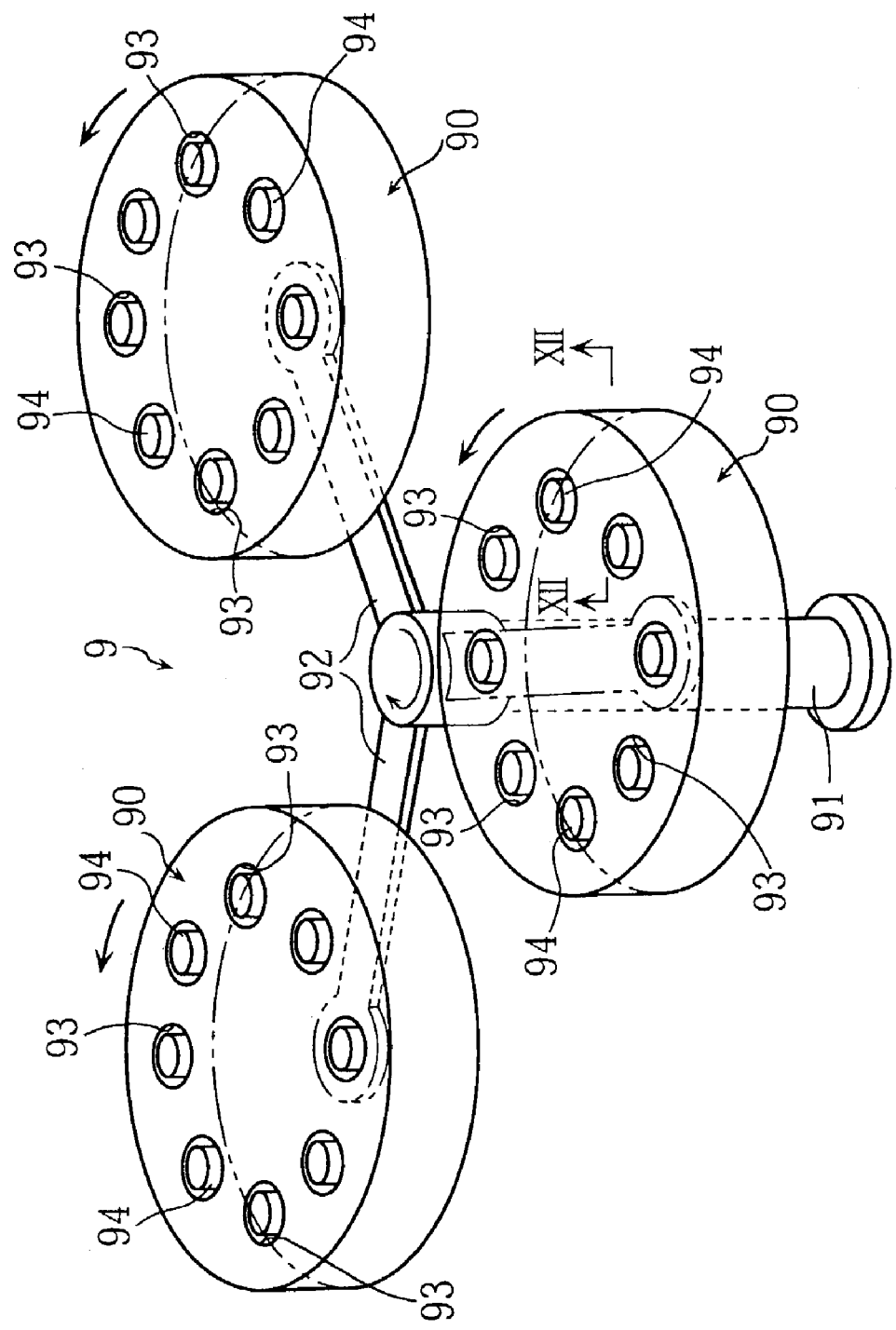
FIG. 12 illustrates a centrifugal separator unit for use in the prior art analyzer.
Figure 13:
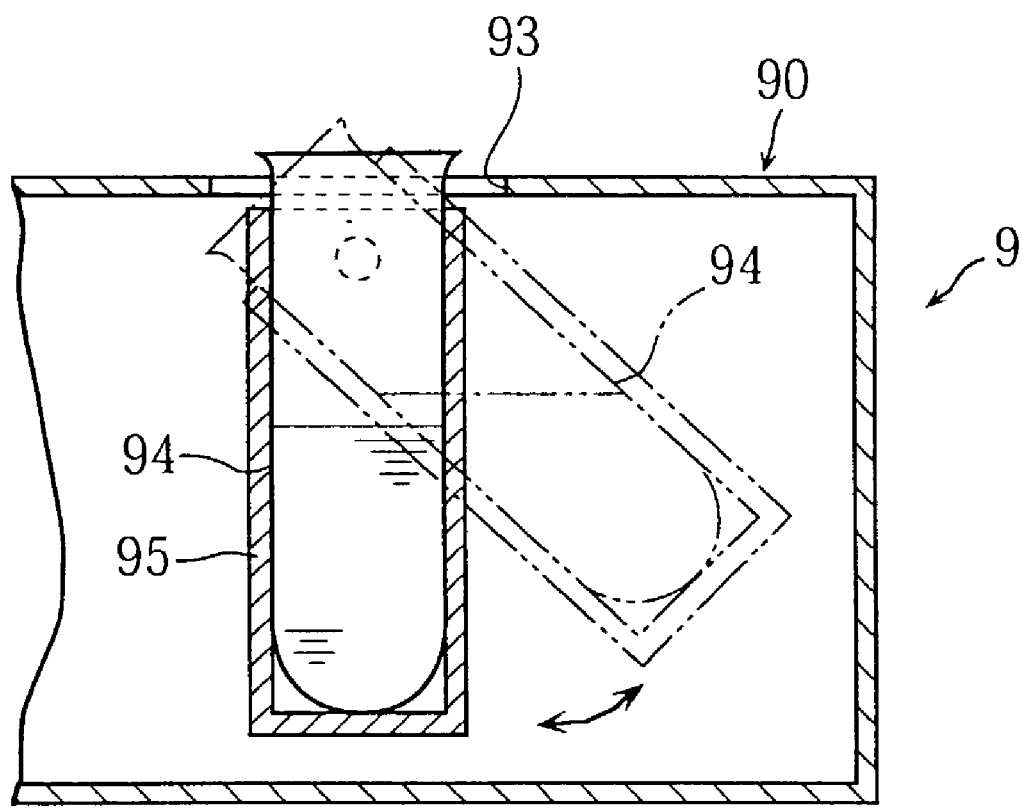
FIG. 13 is a sectional view taken along lines XII—XII in FIG. 12.

As shown in FIG. 9, the slide table 24' is provided with a pair of guide rails 24A'. As shown in FIGS. 7 and 10, each of the guide rails 24A' include two flat surfaces 24a' and 24b' which differ from each other in height, and an inclined surface 24C' connecting the flat surfaces.

Figure 8A:
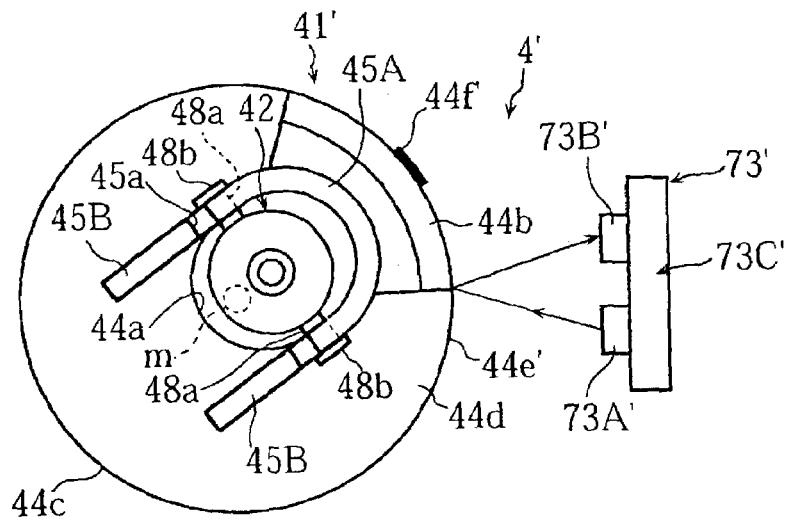
FIGS. 8A–8C illustrate positional controlling of the rotor used for the analyzer of the second embodiment.
Figure 8B:
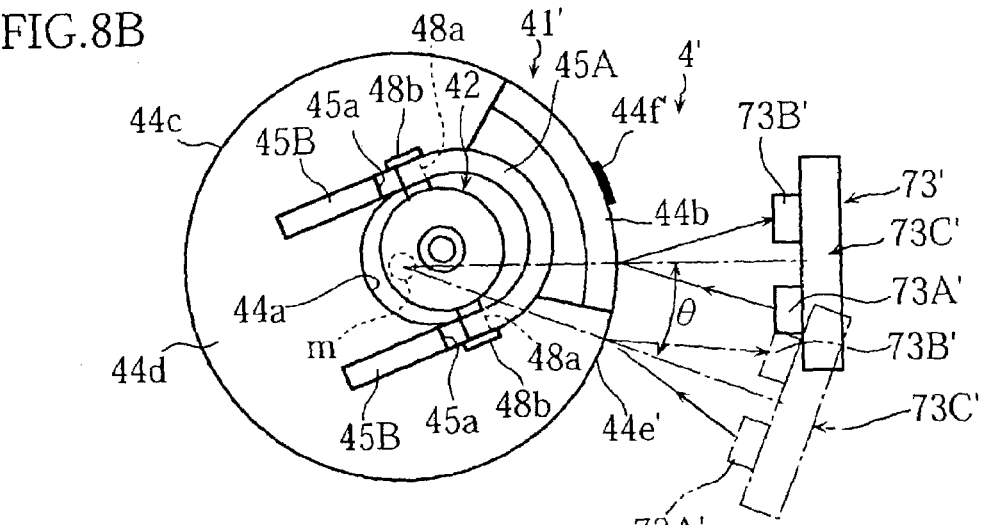
Figure 8C:
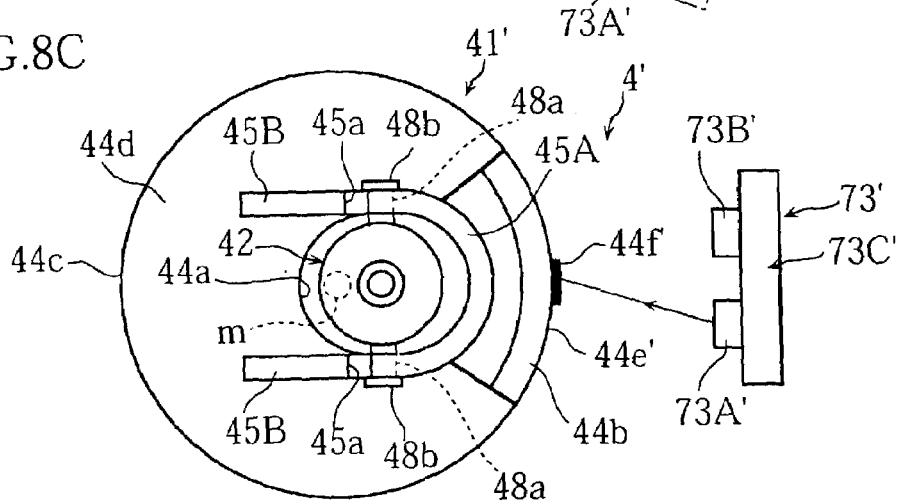

As shown in FIGS. 8A–8C, the rotor 41' has a side surface 44e' provided with a mark 44f' formed of a material having high light absorptivity or high light scattering ability. The side surface 44e' is further provided with an engagement hole 43a' which widens as it extends downward. The rotor 41' is connected to a DC motor M1. In the second embodiment, controlling means (not shown) is provided to intermittently supply DC current (voltage) to the DC motor M1. Therefore, as shown in FIGS. 8A and 8B, the rotor 41' can turn intermittently by a predetermined angle θ.

The rotor 41' suspend a cuvette 42. When the rotor 41' is not rotated, the axis of the cuvette 42 is offset from the rotation axis of the rotor 41' by a predetermined distance (See FIG. 8A). With such a structure, a predetermined centrifugal force can be exerted to the blood in the cuvette 42 during the rotation of the rotor 41' more easily as compared with the case where the axis of the cuvette 42 coincides with the rotation axis of the rotor 41'. Therefore, the centrifugal separation of blood can be performed properly even when the rotor 41' is rotated at a relatively low speed. Since the rotation speed can be decreased, the driving voltage can also be decreased, which leads to a reduction in the running cost.

As described above, the axis of the cuvette 42 is offset from the rotation axis of the rotor 41'. With such a structure, if no countermeasure is taken, the cuvette 42 may stop at different positions every time when the centrifugal separation is completed. In such a case, the sucking of blood plasma with the pipette unit 5 (See FIG. 2) may not be performed properly.

To avoid such a problem, the centrifugal separator 4' of the second embodiment is provided with a positioning mechanism 72' for making the cuvette 42 stop at the same position every time when the centrifugal separation is completed. The positioning mechanism 72' includes detecting unit 73' and a stopper member 74'.

As shown in FIGS. 7 and 8A–8C, the detecting unit 73' includes a light emitting element 73A' and a light receiving element 73B'. The light emitting element 73A' may comprise an LED, whereas the light receiving element 73B' may comprise a photoelectric conversion element. The light emitting element 73A' and the light receiving element 73B' are mounted on a substrate 73C' in facing relationship to a side surface 44e' of the rotor 41'. The substrate 73C' is fixed to the casing 40'. The light emitting element 73A' irradiates the side surface 44e' of the rotor 41' with light, whereas the light receiving element 73B' receives the light reflected by the side surface 44e'. When the light emitted from the light emitting element 73A' is incident on the mark 44f', the light is absorbed or scattered at the mark 44f', so that the amount of light received by the light receiving element 73B' decreases. The light receiving element 73B' outputs signals of a level corresponding to the received amount of light and transmits the signals to information processing means (not shown). Thus, the information processing means determines that the mark 44f' has passed in front of the detecting unit 73' or that the mark 44f' is positioned in front of the detecting unit 73'.

As will be easily understood, the detecting unit 73' can be used not only for detecting the rotational position of the rotor 41' but also for counting the number of rotations of the rotor. Such a structure is advantageous in terms of a cost, because two different kinds of physical values can be measured by a single detecting unit.

As clearly shown in FIGS. 7, 9 and 10, the stopper member 74' includes a support portion 74A'. The support portion 74' has a lower portion rotatably supporting a pair of rotary members 74B' and an upper portion to which a pin 74C' is fixed.

As shown in FIG. 7, the support portion 74A' extends through a through-hole 49a' provided in a bottom wall 49' of the casing 40' to partially project outward from the casing 40'.

Each of the rotary members 74B' is rotatable for movement along the flat surfaces 24a', 24b' and the inclined surface 24c' of the guide rail 24A'.

The pin 74C' extends through a through-hole 74a' of a guide fin 75' fixed in the casing 40'. Between the guide fin 75' and the support portion 74A' is arranged a coil spring 76'. Thus, the support portion 74A' is biased downward (toward the slide table 24') to keep the rotary members 74B' in contact with the guide rails 24A'.

With the above-described structure, when the casing 40' moves, the rotary members 74B' move together with the casing 40' in engagement with the guide rails 24A'. During the movement, the pin 74C' moves upward or downward in accordance with the partial height variation of the guide rails 24A'. For example, when the stopper member 74' moves from right to left of FIG. 10, the pin 74C' moves upward as the rotary members 74B' ascends the inclined surfaces 24c'. When the stopper member moves in the opposite direction, the pin 74C' moves downward as the rotary members descend the inclined surfaces 24c'. In this way, the pin 74C' (i.e. the stopper member 74') is vertically movable in accordance with the movement of the casing 40'. As shown in FIG. 7, the upper end of the pin 74C' is lower than the bottom surface of the rotor 41' when the rotary members 74B' are located on the lower flat surfaces 24b'. On the other hand, the upper end of the pin 74C' is higher than the bottom surface of the rotor 41' when the rotary members 74B' are located on the higher flat surfaces 24a'.

As shown in FIG. 7, the engagement hole 43a' is so provided that its axis generally coincides with that of the pin 74C' when the mark 44f' faces a counterpart surface 73c' of the substrate 73C'. Therefore, when the pin 74C' is moved upward in a state where the axis of the pin 74C' generally coincides with that of the engagement hole 43a', the tip end of the pin 74C' is inserted into the engagement hole 43a', as shown in FIGS. 7 and 9. Thus, the rotor 41' is locked. Since the engagement hole 43a' widens as it extends downward, the insertion of the pin 74C' into the engagement hole 43a' can be performed reliably.

With the positioning mechanism 72', the rotor 41' is positioned so that the mark 44f' faces the substrate 73C' after the centrifugal separation is completed. The details are as follows.

First, as shown in FIGS. 7 and 8A, light emitted from the light emitting element 73A' is directed to the side surface 44e' of the rotor 41' and the reflected light is received by the light receiving element 73B'. At that time, when the mark 44f' does not face the substrate 73C', pulse voltage is supplied to the DC motor M1 to turn the rotor 41' only through the angle θ, as shown in FIGS. 7 and 8B. The pulse width (pulse duration) may be about 20–30 msec, for example, and the rotor 41' may be turned through about 10 degrees, for example.

After the rotor 41' is turned, the side surface 44e' of the rotor 41' is again irradiated with light emitted from the light emitting element 73A' and the reflected light is received by the light receiving element 73B'. At that time, when the mark 44f' faces the substrate 73C' as shown in FIG. 8C, the driving of the rotor 41' by pulse voltage is finished. On the other hand, when the mark 44f' does not face the substrate 73C', pulse voltage is supplied to the DC motor M1 to further turn the rotor 41' only through the angle θ in a manner similar to the above and as shown in FIGS. 7 and 8B. Such pulse driving is repeated until the mark 44f' faces the center of the substrate 73C'.

The irradiation by the light emitting element 73A' and the detection of the reflected light by the light receiving element 73B' may be performed continuously or intermittently until the rotor 41' is properly positioned.

After the mark 44f' is made to face the substrate 73C', the rotor 41' is locked by the stopper member 74' to keep the facing relation. The locking of the rotor 41' is performed by moving the casing 40' from right to left of FIGS. 7 and 10. The movement of the casing 40' is performed by the driving mechanism 23 (See FIG. 7).

After the rotor 41' and the cuvette 42 retained by the rotor 41' are positioned properly, the supernatant liquid in the cuvette 42 is taken by using the pipette unit 5 and applied to a reagent pad 71 of the test piece 7, and the degree of color reaction on the reagent pad 71 is detected by the optical measurement unit 6, as described with reference to FIG. 2. In this way, the concentration of a particular component can be measured.

The present invention being thus described, it is apparent that the same may be varied in many ways. Such variations should not be regarded as a departure from the spirit and scope of the present invention, and all such modifications as would be obvious to those skilled in the art are intended to be included within the scope of the following claims.

The invention claimed is:

1. A centrifugal separator comprising:
    a driving source;
    a rotor rotatable about a rotation axis by the driving source; and
    a swing member including an accommodation space for retaining a liquid analyte to be separated, the swing member being pivotally suspended by the rotor; wherein the rotor has a center of gravity which is offset from the rotation axis, the rotor and the swing member constituting an assembly whose center of gravity coincides with the rotation axis only when the rotor is rotated while pivoting the swing member through a predetermined angle with a predetermined amount of separation liquid analyte contained in the accommodation space.

2. The centrifugal separator according to claim 1, wherein the swing member is removable from the rotor.

3. The centrifugal separator according to claim 2, wherein the swing member is provided with a pair of shaft portions projecting therefrom whereas the rotor is provided with an engagement member for engagement with the shaft portions.

4. The centrifugal separator according to claim 3, wherein the engagement member includes a pair of guides spaced from each other, each of the guides including a cutout for receiving the shaft portion and an inclined surface connected to the cutout.

5. The centrifugal separator according to claim 1, wherein the swing member includes an upper opening and a bevel portion tapering toward the upper opening.

6. The centrifugal separator according to claim 5, wherein the swing member includes a container defining the accommodation space and a lid attached to the container, the upper opening being formed at the lid, the lid including a rim which is connected to the upper opening and which has a constant diameter.

7. The centrifugal separator according to claim 1, wherein the rotor is provided with a stopper for restricting a pivot angle of the swing member relative to the rotor.

8. The centrifugal separator according to claim 1, wherein the swing member has a vertical axis which coincides with the rotation axis of the rotor when the rotor is not rotated.

9. The centrifugal separator according to claim 1, wherein the swing member has a vertical axis which is offset from the rotation axis of the rotor when the rotor is not rotated.

10. The centrifugal separator according to claim 1, wherein the rotor includes a bottom surface, and a side surface formed with a cutout.

11. The centrifugal separator according to claim 1, further comprising a detecting unit for detecting the number of rotations of the rotor and a determination unit for determining whether or not the center of gravity of the rotor during the rotation is offset from the rotation axis based on data obtained by the detecting unit.

12. The centrifugal separator according to claim 11, wherein the determination unit determines that the center of gravity is offset when the number of rotations of the rotor has not reached a predetermined value after lapse of a predetermined time since the rotor started to rotate.

13. The centrifugal separator according to claim 11, further comprising a stopping unit for stopping the rotation of the rotor when the determination unit determines that the center of gravity of the rotor during the rotation is offset.

14. A centrifugal separator comprising:

a driving source;

a rotor rotatable about a rotation axis by the driving source; and a swing member including an accommodation space for retaining a liquid analyte to be separated, the swing member being pivotally suspended by the rotor;

wherein the swing member includes an upper opening and a bevel portion tapering toward the upper opening.

15. A centrifugal separator comprising:

a driving source;

a rotor rotatable about a rotation axis by the driving source; and a swing member including an accommodation space for retaining a liquid analyte to be separated, the swing member being pivotally suspended by the rotor;

wherein the swing member has a vertical axis which coincides with the rotation axis of the rotor when the rotor is not rotated.

16. A centrifugal separator comprising:

a driving source;

a rotor rotatable about a rotation axis by the driving source;

a swing member including an accommodation space for retaining a liquid analyte to be separated, the swing member being pivotally suspended by the rotor; and a detecting unit for detecting the number of rotations of the rotor and a determination unit for determining whether or not the center of gravity of the rotor during the rotation is offset from the rotation axis based on data obtained by the detecting unit.

* * * * *